(12) United States Patent
Kaneko et al.

(10) Patent No.: US 6,398,719 B1
(45) Date of Patent: Jun. 4, 2002

(54) TUBE FOR SPERM WASHING AND CONCENTRATION AND METHOD FOR SPERM WASHING AND CONCENTRATION

(75) Inventors: Satoru Kaneko, Ichikawa; Tadatoshi Uchida, Osaka, both of (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/496,350

(22) Filed: Feb. 2, 2000

(30) Foreign Application Priority Data

Feb. 2, 1999 (JP) .......................................... 11-025428

(51) Int. Cl.[7] .............................. H61D 7/00; B01L 11/00
(52) U.S. Cl. .............................. 600/33; 600/35; 422/101
(58) Field of Search ................................. 210/807, 445, 210/764; 436/178; 422/100, 102, 101, 103; D9/436; 600/33, 35

(56) References Cited

U.S. PATENT DOCUMENTS

| 3,750,645 A | | 8/1973 | Bennett et al. ............. 128/2 G |
|---|---|---|---|
| 4,981,654 A | | 1/1991 | Kuntz et al. ................. 422/102 |
| 5,013,459 A | * | 5/1991 | Gettings et al. ............ 210/764 |
| 5,079,170 A | * | 1/1992 | Rosman et al. ............. 436/178 |
| 5,575,914 A | * | 11/1996 | Jeyendram ................... 210/445 |
| 5,824,272 A | * | 10/1998 | Uchida ........................ 422/102 |
| 5,840,502 A | | 11/1998 | Vlasselaer ................. 435/7.21 |
| 5,976,389 A | * | 11/1999 | Zavos ........................ 210/807 |
| 6,066,297 A | * | 5/2000 | Torti et al. .................. 422/100 |

* cited by examiner

*Primary Examiner*—Eric F. Winakur
*Assistant Examiner*—Nikita R Veniaminov
(74) *Attorney, Agent, or Firm*—Kubovcik & Kubovcik

(57) ABSTRACT

A tube for sperm washing and concentration. The tube is a glass tube 1 having an open end 11 and a bottom portion with a small diameter 12, and an elastic bladder 2 removably provided at the open end 11 of the tube 1. A vulnerable section 13 may be further provided to enable the bottom with small diameter 12 to be easily bent and cut. Contamination of the sperm by bacteria and remaining density gradient carrier are not caused.

5 Claims, 3 Drawing Sheets

TUBE FOR SPERM WASHING AND CONCENTRATION AND METHOD FOR SPERM WASHING AND CONCENTRATION

FIELD OF THE INVENTION

The present invention relates to a tube for sperm washing and concentration and to a method using the tube in order to wash and concentrate sperm collected from humans which is then used to contribute to assisted reproduction technology (ART).

BACKGROUND OF THE INVENTION

The reasons for male infertility are various, but about 90% is due to poor semen quality resulting from idiopathic dysfunction of spermatogenesis. The treatment methods for male infertility are roughly classified into surgical treatment, pharmacotherapy for activation of spermatogenesis and ART. The surgical treatment includes methods such as high ligature in varicocele spermophlebectasia, seminal duct anastomosis in obstructions of the seminal tract and the like which have produced good results in the urological field. However, the effectiveness of the pharmacotherapy is not high in the case of poor semen quality, and the treatment faces hard going. Therefore, ART has been put to practical use for the treatment of male infertility. ART broadly means performing fertilization, medically assisting formation of gamete, fertilization, implantation and maintaining pregnancy. Practically, this means mostly fertilization by artificial insemination from intra-uterine insemination (IUI) to in vitro fertilization embryo transfer (IVF-ET) and further to micro-fertilization.

The number of sperm in semen ejaculated into the vagina decreases as it climbs up within the female genital tracts such as the cervical canal, uterine cavity and uterine tube. Finally, about 10 sperm reach the ampulla of the uterine tube where fertilization takes place. The meaning of semen quality becoming worse means a decrease in the number of sperm reaching the place of fertilization. Therefore, study and treatment of ART have two directions. One is improvement of the method for insemination by providing the sperm as close as possible to the oocyte by by-passing the climbing of sperm up the female genital tract, in order to enable fertilization with as few sperm as possible. In IUI, the cervical canal is by-passed. In IVF-ET, the oocyte ovum is taken out from the body and fertilized in vitro. Further in intra-cytoplasma sperm injection (ICSI), one sperm runs into the cytoplasm of oocyte by perforation, namely, fertilization is also by-passed. In other methods, washing and concentration of the ejaculated semen is attempted in order to provide as many sperm as possible for the insemination.

The most basic function of the sperm is to transport chromosomes. The sperm is functionally classified into the acrosome, sperm head and midpiece-tail. The sperm head includes chromosome. The midpiece-tail is concerned with energy metabolism and sperm motility. And the acrosome is concerned with adhesion and fusion with oocyte ovum. In general, preparation of sperm provided for artificial insemination has, as an objective, selection of progressively motile sperm being in the matured normal state, which is mainly the function of the midpiece-tail.

The sperm immediately after ejaculation has only potential fertility, but obtains the possibility of insemination through physiological and morphological changes such as capacitation, acrosome reaction and the like by culture for some hours in the female genital tract or in vitro. In IVF-ET, because the concentration of the sperm required for insemination is low, it is regarded as the best method for treating oligozoospermia and asthenozoospermia. However, in the case with poor semen quality, it is clinically clear that insemination is impossible because of few motile sperm, which suggests that an understanding of the acrosomal functions, including capability for induction of acrosome reaction, in addition to concentration and motility of sperm (the function of the midpiece-tail) which were previously regarded as an indication for fecundity fertility (namely, the fertility against female) is also important. Further, because ICSI is introduced for a severe case of poor semen quality, it is important to understand in detail the function of sperm as well as estimation of chromosome. Improvement of the method for insemination results in that the number of sperm provided for the insemination is decreased. However, in vitro operations of oocyte ovum and embryo are also required. Further, in the preparation of sperm, it is needed to perform selection of sperm and physiological change of sperm in vitro, instead of in the female genital tract. Therefore, establishment of an improved method for purifying sperm corresponding to the improvement in the method for insemination is indispensable.

The sperm provided for artificial insemination differ in the conditions for preparation according to the method of insemination. Namely, in IUI, sperm concentration is firstly required. In IVF-ET, required sperm concentration is less than that in IUI, but higher techniques such as selection of motile sperm, removal of seminal plasma and bacteria, and the like are also required (the method for sperm washing and concentration). The preparation of sperm is roughly classified into two groups, namely a method by centrifugation and a method by separation caused by the sperm's motility. In the method by centrifugation, density gradient centrifugation was previously employed by using polymerized sucrose, Ficoll, but at present modified colloidal silica gel or Percoll, is used. As the method for insemination, the single-layered "Percoll" method for sperm concentration, the cushion method, the multi-layered "Percoll" method, which, enables the selection of sperm, the continuous-step density gradient centrifugation method and the like are employed. And as the method by separation caused by the sperm's motility, the swim up method is generally employed, but in the case with poor semen quality, the swim down method, which is a variation of the swim up method, is employed.

The density gradient centrifugation method using Percoll is a method comprising, in order to avoid complications in the operation of continuous-step density gradient centrifugation, layering semen directly onto 80% Percoll which is made isotonic and stirring the layers of semen and Percoll to make a continuous density gradient for centrifugation. The motile sperm is concentrated in the sediment.

Sperm loses cytoplasm during its formation and maturation. The matured sperm having motility has a higher density than bacteria and unmatured sperm having cytoplasm. The density gradient centrifugation method using Percoll is carried out by separating the matured motile sperm from seminal plasma and bacteria, based on such a theory.

However, in the prior density gradient centrifugation method using Percoll, because the supernatant is removed by pipetting, etc., after the centrifugation, there is a defect that the concentrated sperm in sediment is contaminated again by the flow of seminal plasma or bacteria attached to the wall of centrifuge tube into the sperm. There is another defect that much Percoll remains because the amount of sediment is as much as 0.1 to 0.2 ml. Also, in artificial insemination with a husband's semen (AIH) by injecting the washed sperm into the uterine cavity, the sediment is required to be diluted again with culture medium and centrifuged at a low rate in order to remove Percoll. As a result, the sperm recovery rate is lowered (concentration of sperm is lowered), and motility of sperm is also lowered. Thus, purification of sperm has difficulties. In the ejaculated semen, fiber of undergarment to which bacteria is attached is also contained. As a result, there is also a problem that sperm is contaminated by fiber which is contained in sediment after centrifugation.

Also, Percoll on the market has a high level of endotoxin. Therefore, such Percoll can not be used for sperm washing, and sperm suspended in Percoll can not be directly added to the embryo culture system for IVF-ET.

The present invention is accomplished in view of the above mentioned background. An object of the present invention is to provide a method for sperm washing and concentration and a tube for sperm washing and concentration by which contamination by bacteria and remaining Percoll are not caused.

An object of the present invention is also to provide a method for sperm washing and concentration and a tube for sperm washing and concentration by which a high sperm recovery rate without lowered sperm motility is obtained.

Another object of the present invention is to provide a method for sperm washing and concentration and a tube for sperm washing and concentration by which endotoxin can be removed effectively.

SUMMARY OF THE INVENTION

As the result of extensive investigations in order to solve the above mentioned problems, the present inventors found that the flow of supernatant can be inhibited by providing a small diameter portion at the bottom of the centrifuge tube in order to concentrate sperm at the bottom portion having a small diameter by centrifugation and, after centrifugation, by bending and cutting of the bottom portion having the small diameter under a condition that reduced pressure is kept in the centrifuge tube. Thence, the present invention has been accomplished.

Namely, the present invention relates to a tube for sperm washing and concentration comprising a tube having an open end and a bottom portion with a small diameter, and an elastic bladder removably provided at the open end of the tube. Herein, a vulnerable or weakened part may be further provided to easily bend and cut the bottom portion having the small diameter.

The present invention also relates to a method for sperm washing and concentration comprising the steps of:

i) filling the above mentioned glass tube for sperm washing and concentration with a density gradient carrier, ii) sucking up semen diluted with the same volume of HANKS solution or physiological saline into a syringe, iii) gently discharging the semen of step ii) onto a removing filter; removing fiber, gelatin-like mass and urolithiasis therein by the removing filter; and layering the filtrated semen onto the density gradient carrier in the glass tube, iv) after layering the whole volume of the semen onto the density gradient carrier, stirring both sides of the interface between the semen and the density gradient carrier to cause the interface to disappear, v) centrifuging the glass tube of step iv), vi) after the centrifugation, providing the elastic bladder in a compressed state at the open end of the glass tube and obtaining the sediment containing the washed and concentrated sperm and the density gradient carrier by bending and cutting the bottom portion having a small diameter of the glass tube, and vii) removing the layer of the density gradient carrier so as to leave only the sediment.

Herein, as the density gradient carrier, modified colloidal silica (Percoll) or polymerized sucrose (Ficoll) and the like are exemplified. Preferably, the Percoll is treated to remove endotoxins and then is added to culture medium to make it isotonic and has a 90 to 98% concentration. In the present invention, "Percoll" means colloidal silica sol with polyvinyl pyrrolidone coating.

The condition of centrifugation may be variously selected according to the desired object, and is generally 1.000×g, for 20 to 30 minutes.

DETAILED DESCRIPTION OF THE PREFERRED EMBODIMENTS

Firstly, the tube for sperm washing and concentration of the present invention is explained by reference to FIGS. 1 and 2.

Figure 1:
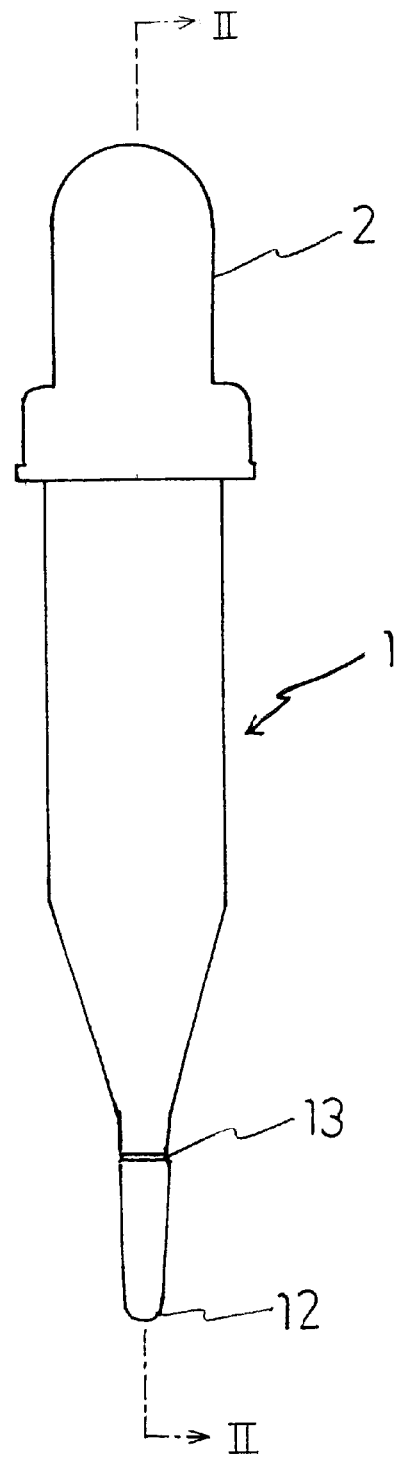
FIG. 1 is a plan view showing one embodiment of the tube for sperm washing and concentration of the present invention.

FIG. 1 is a plan view showing one embodiment of the tube for sperm washing and concentration of the present invention. FIG. 2 is a cross-sectional view along II—II of the tube shown in FIG. 1.

Figure 2:
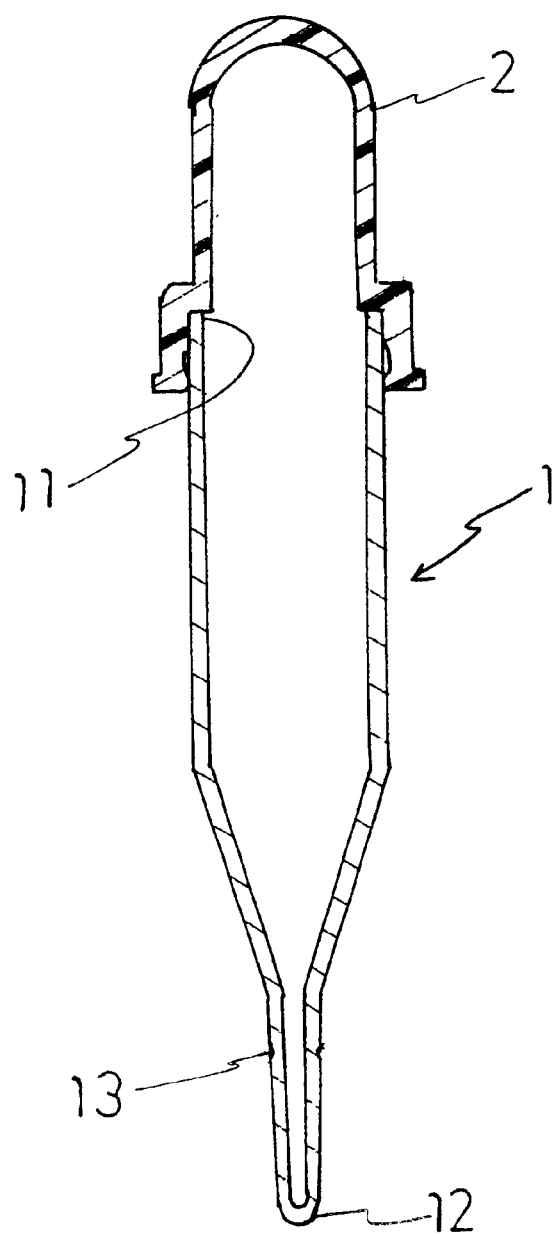
FIG. 2 is a cross-sectional view from II—II of the tube shown in FIG. 1.

As shown in FIG. 1 and FIG. 2, the tube for sperm washing and concentration of the present invention comprises a glass tube 1 having a top portion with an open end 11 and a closed bottom portion 12 with a reduced or smaller diameter relative to the top portion of the tube (hereinafter simply referred to as bottom with small diameter 12), and an elastic bladder 2 to be provided at the open end 11 of the tube 1. Herein, a weakened or vulnerable part (cut part) 13 may be further provided in the bottom with small diameter 12 to enable the bottom with small diameter 12 to be easily bent and cut.

The tube 1 has the open end 11 and the bottom with small diameter 12. Because the whole tube is made of glass, it is possible to carry out heat sterilization at about 300° C. for 1 hour in order to inactivate the organic contamination substances such as endotoxin. Also, because the tube is made of glass, the bottom 12 can be bent and cut after centrifugation. The size of the tube 1 may be 5 to 20 mm in inner diameter of the open end 11 and 40 to 170 mm in length. The size of the bottom 12 may be 15 to 40 mm in length and 2 to 7 mm in inner diameter. According to the amount of sperm (usually 5 to 10 µl), the cut part (the vulnerable part) 13 is preferably provided at a position about 10 to 30 mm from the bottom of the tube 1.

In FIG. 1 and FIG. 2, the elastic bladder 2 is provided at the open end 11 of the glass tube 1 and can be removable therefrom. In collecting of sperm, the elastic bladder 2 is provided at the open end 11 of the tube 1, compressed by fingers of an operator and released from the compressed state. Then, the original shape of elastic bladder 2 is restored by its elasticity and reduced pressure is caused in the tube 1.

And when the bottom with small diameter 12 is bent and cut to open the bottom, the liquid (supernatant) contained in the tube 1 at a higher position than the bent and cut part is inhibited from flowing because of the reduced pressure. Also, sperm existing in the bottom of the tube is concentrated into about 5 to 10 μl of volume in sediment by the centrifugation. Therefore, it is possible to leave the sediment only by removing the layer of the Percoll. In the case that the sperm is resuspended in a culture medium according to the object, the inclusion of Percoll can be minimized because of the small diameter of the tube.

Figure 3:
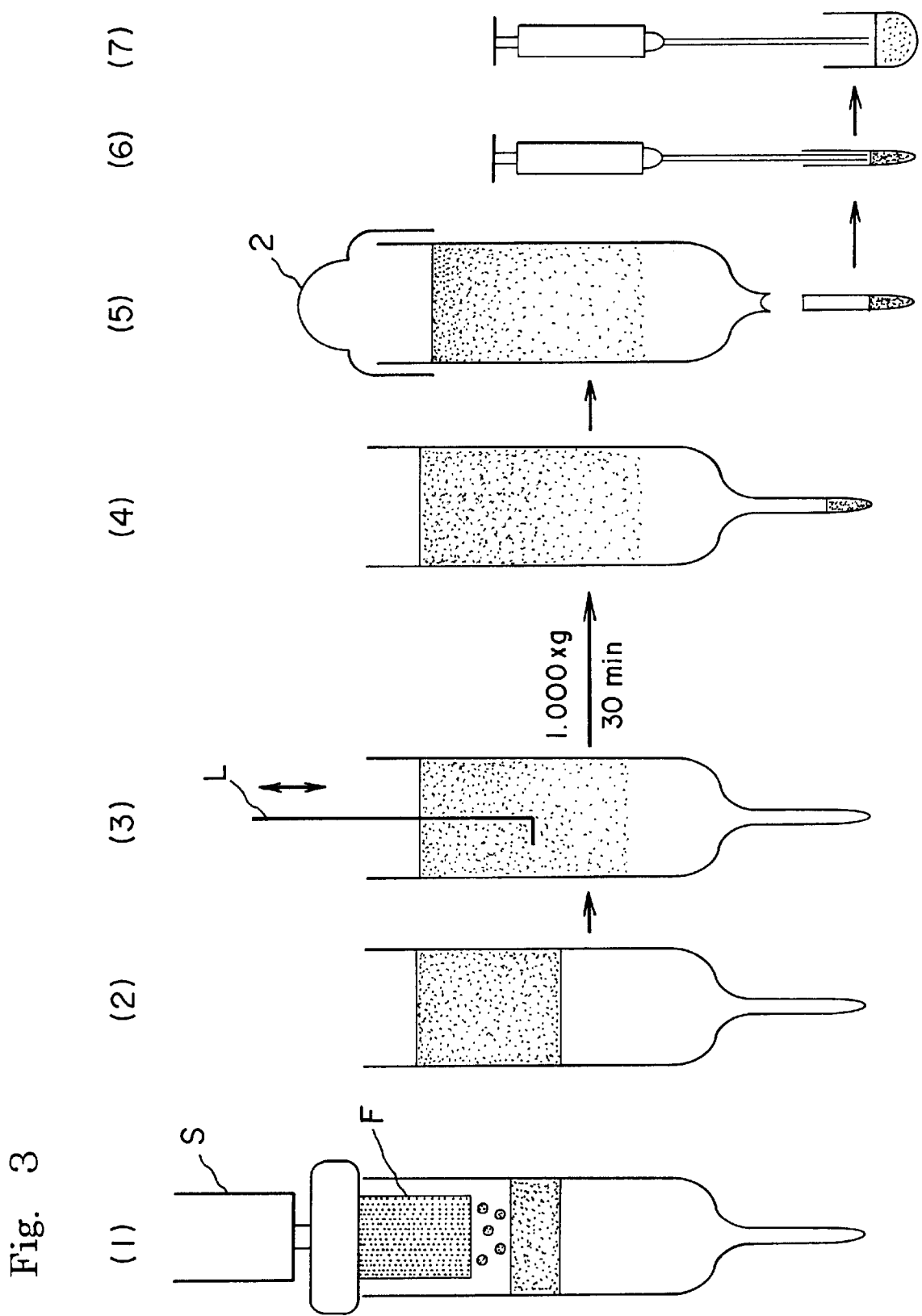
FIG. 3 is a figure explaining the use of the tube for sperm washing and concentration shown in FIG. 1.

Next, the method for sperm washing and concentration of the present invention is explained by reference to FIG. 3.

Firstly, semen is sampled, confirming the name, the number of patient's chart and the like, and observed grossly as to appearance (to check for hematospermia and the like). Then, confirming the name of the patient, semen is sucked up into a 5 ml disposable syringe, the amount thereof measured, and is then sucked up and discharged several times by a syringe in order to liquefy and homogenize the semen. After the liquefaction and homogenization of the semen, semen is dropped onto a slideglass to observe the number and motility of sperm. Then, the condition of liquefaction of semen and containing of gel are observed. On the other hand, the tube 1 for sperm washing and concentration of the present invention is filled with the Percoll which is made isotonic and has a 90 to 98% concentration (step i). Then, semen is mixed with the same volume of HANKS solution or physiological saline and repeatedly sucked up and discharged by a syringe S to dilute it, and the diluted semen is sucked up into the syringe S (step ii). The semen is gently discharged on the removing filter F which is inserted into the open end 11 of the tube 1 to remove fiber, gelatin-like mass, urolithiasis and the like therein by the removing filter F (FIG. 3–1), and the filtrated semen is layered onto the Percoll ((step iii), FIG. 3–2). After layering the whole volume of the semen onto the Percoll, both sides of the interface between the semen and the Percoll in the tube 1, usually a distance of 2 cm from both sides, are stirred by, for example, an L shaped rod, to remove the interface ((step iv), FIG. 3—3).

Then, the tube 1 is centrifuged, for example at 3000 rpm (1.000×g) for 20 to 30 minutes. By centrifugation, sperm is concentrated at the bottom with small diameter 12 of the tube 1 ((step v), FIG. 3–4). After the centrifugation, an elastic bladder 2 in the compressed state is provided at the open end 11 of tube 1, and then sperm is obtained by bending and cutting the bottom with small diameter 12 at the cut part 13 ((step vi), FIG. 3–5). Upon the bending and cutting of the glass, in order to avoid injuries thereby, it is preferable to carefully bend and cut the glass, providing a tip for the use (not shown in FIG. 3) thereof at the lower position of the tube 1. Because the obtained sperm is concentrated in about 10 μl at the bottom of the tube, only the sediment is left by removing the layer of the Percoll as much as possible ((step vii), FIG. 3–6). According to the desired object, the sperm may be resuspended in a culture medium (FIG. 3–7). The upper part of the tube 1 and the supernatant are disposed, but the elastic bladder 2 can be used repeatedly, and then washed and kept.

EXAMPLE 1

Human semen sampled by self was maintained at room temperature for about 30 minutes for liquefaction, observed as to general semen quality, washed and concentrated according to the method of the present invention (3000 rpm/min, 20 minutes) and concentration of sperm, motility of sperm and activity of acid phosphatase (Acid P) measured. The results as shown in Table 1 were obtained.

Temperature during the observation was kept at 37° C. by using a transparent incubation disk for a microscope stage, and the concentration of sperm was measured by using a Makler sperm calculation disk. The motility of sperm (motility, motile rate) was observed by applying 10 μl of semen on a chamber treated human serum albumin for the observation of the motility of sperm, and measured by a computer imaging analysis device (CASA 3000, manufactured by Cell Soft). And, the activity of acid phosphatase was measured by Acid Phosphatase KII Test Wako (manufactured by Wako Chemicals) as a reagent for measurement of the activity of acid phosphatase (Acid P) and 4.6 mmol disodium phenyl phosphate as a substrate, at 37° C.

TABLE 1

|  | Original semen | Washed and concentrated sperm suspension |
|---|---|---|
| Concentration of sperm (sperm/ml) | $35 \pm 26 \times 10^6$ | $2247 \pm 1203 \times 10^6$ |
| Motility (%) | $38.4 \pm 11.8$ | $68.8 \pm 15.4$ |
| Motile rate of sperm (μm/sec) | $28.8 \pm 7.23$ | $30.8 \pm 6.36$ |
| Acid P (KA unit/ml) | $25.8 \pm 23.4 \times 10^4$ | $12.4 \pm 9.45$ |

Note:
Amount of original semen was $2.4 \pm 1.1$ ml. After washing and concentrating according to the present method, the sperm suspension was resuspended in HANKS solution to a volume of 10 ml.

In the present method, considering that immature sperm has worse motility and fertility because it contains much cytoplasm, only matured sperm having better motility and fertility of which cytoplasm is lost is selectively recovered. As a result, a dozens-fold concentration of sperm was obtained as shown in Table 1. The motility of sperm was also improved by washing. The removing rate of seminal plasma, comparing the activity of acid phosphatase of the obtained semen with that of original semen, was significantly reduced. Therefore, it is considered that seminal plasma could be removed completely by washing.

As explained above, it is clear that insemination rate can be improved according to the present invention because sperm having high motility is selectively recovered with a high recovery rate of sperm.

What is claimed is:

1. A method for sperm washing and concentration comprising the steps of:
   i) providing a tube for sperm washing and concentration comprising a glass tube having a top portion and a bottom portion, an open end being provided in the top portion and the bottom portion being closed and having a reduced diameter relative to said top portion, and an elastic bladder removably provided at the open end of the tube, wherein said bottom portion having a reduced diameter has a weakened portion for bending and removing said bottom portion,
   ii) filling the rube for sperm washing and concentration with a density gradient carrier,
   iii) diluting semen with an equivalent volume of HANKS solution or physiological saline,
   iv) providing the semen of step iii) onto a filter for removing fiber, gelatin-like mass and urolithiasis therein and layering the filtrated semen onto the density gradient carrier in the glass tube, v) after layering the whole volume of the semen onto the density gradient carrier, stirring both sides of an interface between the semen and the density gradient carrier to remove the interface, vi) centrifuging the tube of step v), vii) after the centrifugation, providing said elastic bladder in a compressed state at the open end of the glass tube and obtaining a sediment containing the washed and concentrated semen and the density gradient carrier by removing the bottom portion with a small diameter of the tube, and viii) removing the density gradient carrier to leave essentially only the sediment.

2. The method for sperm washing and concentration according to claim 1, wherein the density gradient carrier is colloidal silica or polymerized sucrose.

3. The method for sperm washing and concentration according claim 1, wherein the density gradient carrier, prior to being filled into the glass tube is treated to remove endotoxin and is then added to a culture medium and made isotonic and has a 90 to 98% concentration.

4. The method for sperm washing and concentration according to claim 1, wherein the density gradient carrier is colloidal silica having a polyvinyl pyrrolidone coating.

5. The method for sperm washing and concentration according claim 4, wherein the density gradient carrier, prior to being filled into the glass tube is treated to remove endotoxin and is then added to a culture medium and made isotonic and has a 90 to 98% concentration.

* * * * *